United States Patent [19]

Williams, Jr. et al.

[11] Patent Number: 5,406,503
[45] Date of Patent: Apr. 11, 1995

[54] CONTROL SYSTEM FOR CALIBRATING AND DRIVING ULTRASONIC TRANSDUCER

[75] Inventors: Daniel L. Williams, Jr., Florissant; Kevin P. Kepley, Dellwood; John A. Painter, St. Charles, all of Mo.

[73] Assignee: American Cyanamid Company, Wayne, N.J.

[21] Appl. No.: 954,693

[22] Filed: Sep. 30, 1992

Related U.S. Application Data

[63] Continuation of Ser. No. 428,354, Oct. 27, 1989, abandoned.

[51] Int. Cl.$^6$ .................. G01H 11/08; A61B 17/39
[52] U.S. Cl. .................. 364/571.01; 364/483; 73/579; 604/22; 606/34; 606/38
[58] Field of Search .................. 364/571.01–571.08, 364/483, 551.01; 73/579; 128/24.1, 24.5; 604/22; 606/107, 34, 37–40

[56] References Cited

U.S. PATENT DOCUMENTS

| | | | |
|---|---|---|---|
| 2,947,889 | 8/1960 | Rich | 310/26 |
| 3,517,665 | 6/1970 | Sheldon | 128/24 |
| 3,629,726 | 12/1971 | Popescu | 331/116 M |
| 3,772,538 | 11/1973 | Supitilov | 310/9.1 |
| 3,990,452 | 11/1976 | Murry et al. | 128/305 |
| 4,168,447 | 9/1979 | Bussiere et al. | 310/316 |
| 4,169,984 | 10/1979 | Parisi | 310/323 |
| 4,371,816 | 2/1983 | Wieser | 318/118 |
| 4,587,958 | 5/1986 | Noguchi et al. | 128/24 AA |
| 4,633,119 | 12/1986 | Thompson | 310/325 |
| 4,634,420 | 1/1987 | Spinosa et al. | 128/305 |
| 4,635,483 | 1/1987 | Mishiro | 73/579 |
| 4,861,332 | 8/1989 | Parisi | 128/305 |
| 4,867,141 | 9/1989 | Nakada et al. | 128/24 |
| 4,886,060 | 12/1989 | Wiksell | 128/303.14 |
| 4,903,696 | 2/1990 | Stasz et al. | 606/37 |
| 4,966,131 | 10/1990 | Houghton et al. | 128/24 AA |
| 4,989,155 | 1/1991 | Begin et al. | 364/571.06 |
| 5,001,649 | 3/1991 | Lo et al. | 364/484 |
| 5,113,116 | 5/1992 | Wilson | 310/316 |

FOREIGN PATENT DOCUMENTS

| | | | |
|---|---|---|---|
| 0229003 | 7/1987 | European Pat. Off. | |
| 1413440 | 7/1988 | U.S.S.R. | 73/579 |

Primary Examiner—Vincent N. Trans
Attorney, Agent, or Firm—Douglas E. Denninger

[57] ABSTRACT

An electronic control system for determining the resonant frequency of and driving ultrasonic transducers in a phacoemulsification probe used for ophthalmic surgery. The control system includes a voltage control led oscillator, power amplifier, power monitor, and automatic gain control circuit operating under the direction of command signals received from a microprocessor-based control console. The control system operates in a constant apparent power, direct drive mode with closed loop feedback maintaining the electrical power provided to the primary of a RLC transformer at the constant level requested by the command signals from the console. The frequency of the drive signal is held at the dominant resonant frequency of the ultrasonic transducer which is being driven by the control system. This resonant frequency is determined via a calibration procedure performed when the probe is first attached to the control system. During this procedure a constant voltage drive signal is swept through a range of frequencies and the electrical power consumed by the transducer is measured and stored at selected intervals such as 100 Hertz increments. The resonant frequency is also determined in part by looking for the frequency at which maximum power is consumed by the probe. The stored data is also subjected to other tests to check that the peak is indeed a resonant frequency and that the probe has selected output power characteristics about this resonant frequency, thus helping to ensure that the probe is capable of operating satisfactorily when driven by the control system.

15 Claims, 6 Drawing Sheets

CONTROL SYSTEM FOR CALIBRATING AND DRIVING ULTRASONIC TRANSDUCER

This is a continuation of application Ser. No. 07/428,354, filed on Oct. 27, 1989, now abandoned.

BACKGROUND OF THE INVENTION

CROSS-REFERENCE TO RELATED APPLICATIONS

The present invention is related to the subject matter of the following commonly assigned co-pending applications:

Ser. No. 07/251,531 filed Sep. 30, 1988 in the name of Kevin L. Klug and entitled "Phacoemulsification Probe"; and Ser. No. 07/267,713 filed Nov. 4, 1988, which is a continuation of application Ser. No. 06/928,170 filed Nov. 6, 1986 and entitled "Control System For Ophthalmic Surgical Instruments."

The present invention is also related to the subject matter of the following commonly assigned applications being filed concurrently on even date herewith:

Application Ser. No. 428,232, filed Oct. 27, 1989 entitled "Control System For Ophthalmic Surgical Instruments";

Application Ser. No. 428,216, filed Oct. 27, 1989 entitled "Modular Cabinet For Surgical Control System";

Application Ser. No. 428,355, filed Oct. 27, 1989 entitled "Footswitch Assembly With Electrically Engaged Detents"; and Application Ser. No. 428,239, filed Oct. 27, 1989 entitled "Pneumatic Controls For Ophthalmic Surgical System".

The disclosures of each and every one of the above-referenced applications is hereby incorporated herein by reference.

1. Field of the Invention

The present invention relates in general to circuits and methods for calibrating and driving ultrasonic transducers found in phacoemulsification instruments used for ophthalmic surgical procedures, and in particular to calibration methods used to determine the resonant frequency of such ultrasonic transducers and to test such transducers, and to electronic control systems for powering such ultrasonic transducers.

2. Description of Related Art

Phacoemulsification refers to the process of ultrasonic disintegration of the lens of a human or animal eye using a vibrating probe which operates at a frequency above the audio range. It is a well-known and widely used surgical procedure for disintegrating cataracts. The probe includes a hollow needle vibrating at ultrasonic frequencies to shatter the cataract; the shattered debris are withdrawn through the hollow part of the needle. The needle is mounted in an instrument which sometimes is referred to as a phacoemulsification handpiece, phaco handpiece or phaco probe. A number of designs for such handpieces or probes are known, the most common of which utilize piezoelectric transducers to produce the vibrations of the needle at ultrasonic frequencies. Aforementioned application Ser. No. 07/251,531 describes and claims one such phacoemulsification probe that is commercially available from the assignee of the present invention, namely Storz Instrument Company of St. Louis, Mo. (hereinafter "Storz").

Figure 1A:
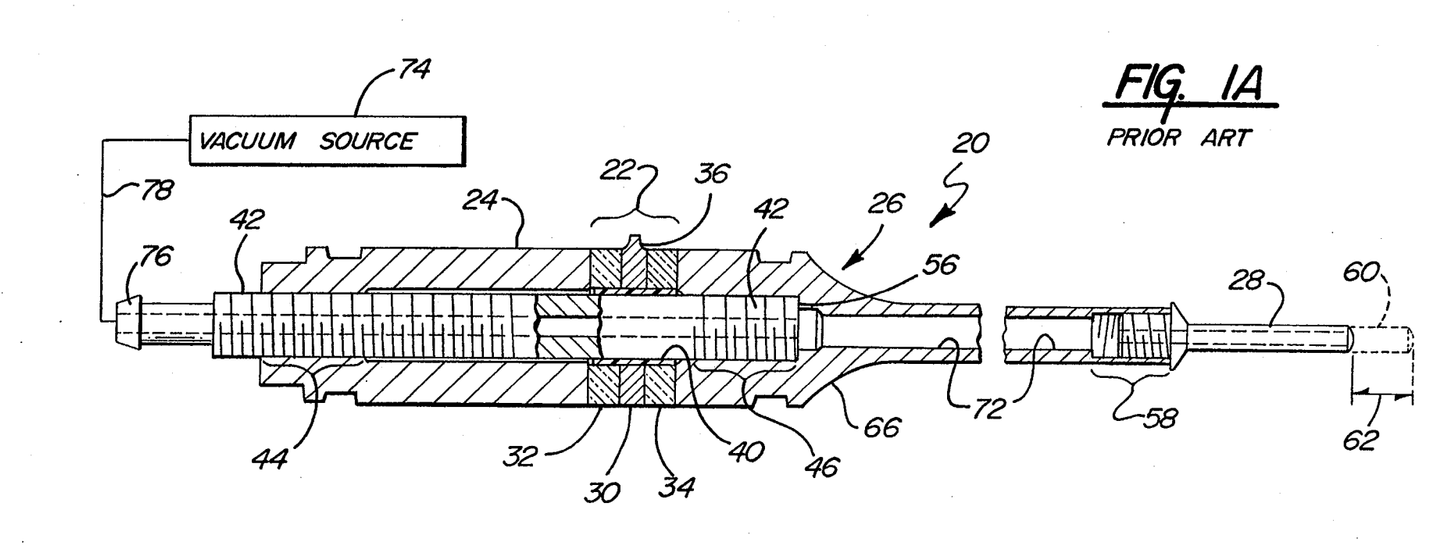
FIGS. 1A and 1B show, in longitudinal cross-section and in exploded perspective view respectively, a prior art phacoemulsification probe including an ultrasonic transducer used in ophthalmic surgical procedures.
Figure 1B:
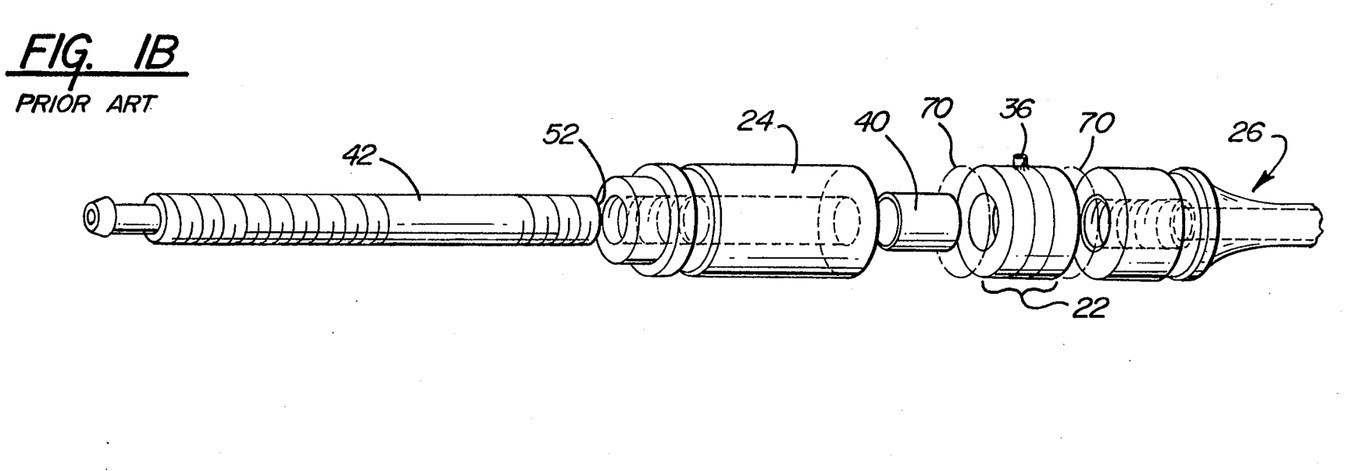

FIGS. 1A and 1B illustrate the construction of the phaco probe disclosed in the aforementioned application Ser. No. 07/251,531. The probe 20 includes an ultrasonic transducer 22 located between a reflector 24 and resonator 26. The transducer 22 includes an electrode 30, constructed of unhardened #01 carbon steel, and two piezoelectric crystals 32 and 34. The crystals 32 and 34 may be constructed, for example, of a modified lead zirconate titanate ceramic material, formed into rings, and silver coated for electrical conductivity. Materials of this type are marketed under the trade name PXE by the Electronic Components and Materials Division of North American Phillips Corporation. An electrical lug 36 fastened to the electrode 30, allows a connection to be made to a power supply. An insulating tube 40 fits within the bore of the transducer 30. The reflector 24 is fastened to the resonator 26 by a hollow threaded tube 42 which mates to the threaded regions 44 and 46 in the reflector and resonator respectively.

Both the hollow tube 42 and the resonator 26 are preferably constructed of 6AL-4V titanium. Reflector 24 is constructed of the #17 tungsten. The insulating sleeve 40 may be made of Teflon. To assemble the components shown in FIG. 1B into the completed assembly 20 shown in FIG. 1A, threaded tube 42 is first threaded into the resonator 26 until the end 52 is seated against the shoulder 56 in the resonator 26. Then the reflector 24 is threaded onto the tube 42 until the transducer is compressed the desired amount.

The phaco probe 20 shown in FIG. 1 may be used as follows. A phacoemulsification needle 28, known in the art, such as Model No. IA-145 available from Storz, is screwed into the threaded end 58 of resonator 26. In use, the needle 28 vibrates in a longitudinal mode by alternately compressing to a retracted position illustrated by solid lines in FIG. 1A and expanding to a extended position illustrated by phantom lines 60. The vibrational displacements, indicated by dimension 62, may be anywhere from about 0.001 inch to about 0.005 inch, depending upon the strength and frequency of the electrical drive signal applied to the transducer. The vibration of the needle nominally occurs at the oscillation frequency of the piezoelectric crystals 32 and 34, which are coupled to the needle 28 through the resonator 26. Curved region 66 of the resonator 26 acts as a horn in order to impedance-match the crystals with the needle 28. Resonator 26, as a whole, functions as a one-quarter wave length transmission line (at the crystal frequency) on which needle 28 acts as a load.

The crystals 32 and 34 in FIG. 1 are driven by a signal applied to the electrode 30 and the reflector 24. The application of an alternating current signal to the crystals 32 and 34 causes them to cyclically expand to the extended position shown by phantom lines 70 in exaggerated form in FIG. 1B, and then contract to the solid position also shown in FIG. 1B. This cyclic expansion and contraction applies mechanical pulses to the resonator 26 at the signal frequency. The vibrating needle 28, when brought near a cataract, causes the cataract to shatter. The shattered debris is withdrawn through the channel 72 of the probe 20 under the influence of a vacuum generated by vacuum source 74 that is attached to the connector 76 by conventional plastic tubing represented by line 78.

As is known in the art, it is possible to construct piezoelectric crystals of various different materials, each of which has a characteristic resonant frequency. The crystal transducer 22 used with the Storz phacoemulsification probes of the type shown in FIG. 1 require a driving signal frequency applied to electrode 30 and reflector 24 in the range of 26.0 KHz to 32.0 KHz for the transducers normally used with the Storz phaco probe shown in FIG. 1. The present application will thus refer to a resonant frequency range between 26 KHz to 32 KHz, but those skilled in the art will appreciate the applicability of the present disclosure to ultrasonic transducers for medical instrument probes which operate at different frequencies.

One system for applying such driving signals to crystals 32 and 34 is described in aforementioned application. Ser. No. 07/251,531, and has been commercially used in the ophthalmic surgical console system from Storz which is sold under the trademark "DAISY."

Figure 2:
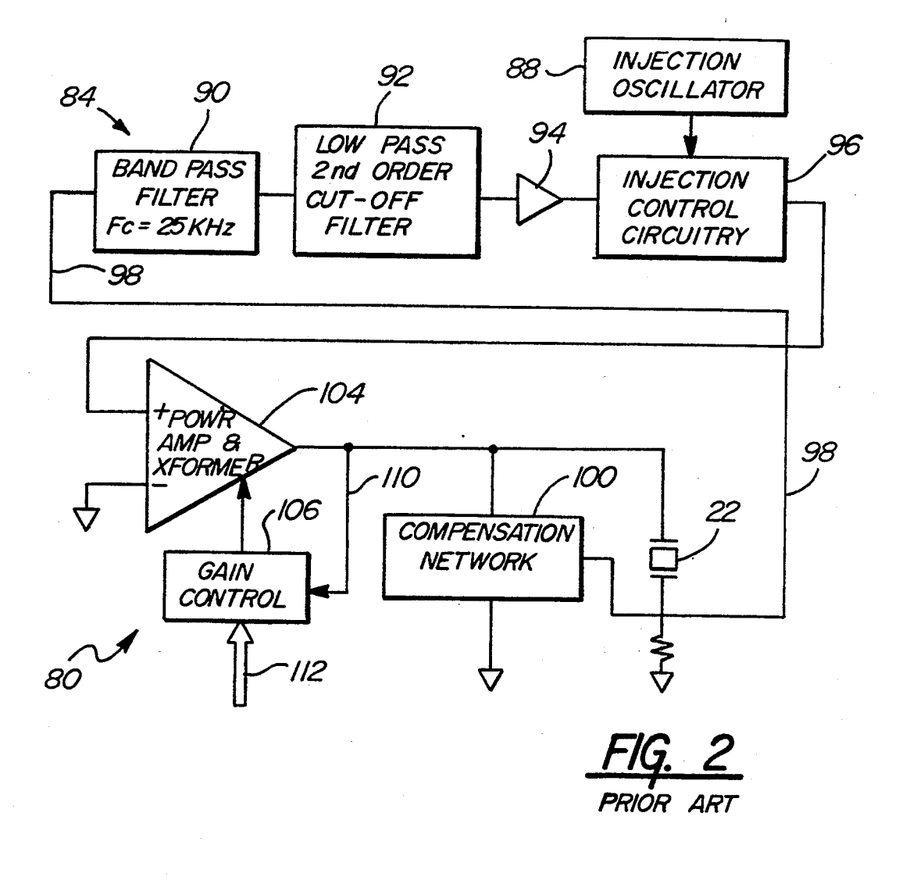
FIG. 2 is a block diagram of a prior art electronic control system for driving an ultrasonic transducer used in ophthalmic surgical procedures.

FIG. 2 presents a block diagram of the driving circuit 80 used in the DAISY console. As is well known, the piezoelectric transducer 22 may be modeled as an RLC series resonant network in parallel with a capacitance when operating under load and near the transducer's resonant frequency. (This model of the transducer is not shown in FIG. 2.) Being a closed loop system, the driving circuit 80 is essentially an oscillator which fulfills the Barkhausen criteria for oscillation, namely it has zero phase shift and unity loop gain. The design frequency of the oscillator may be set at 28.5 KHz plus or minus 0.5 KHz for a transducer which has a nominal resonant frequency around 28.5 KHz. The feedback portion 84 of the closed loop includes an injection oscillator 88, a band pass active filter 90, low pass active filter 92, and a variable gain amplifier 94. The injection oscillator 88 provides an initial voltage signal at a frequency near the transducer resonant frequency to the injection control circuitry 96. That initial signal is disengaged from the loop of the feedback portion 84 by circuitry 96 once the driving circuit 80 provides a signal strong enough to maintain transducer oscillation. The band pass and low pass filters 90 and 92 provide the appropriate frequency selectivity and phase shifts characteristics to maintain the strength of the transducer feedback signal while the transducer phase characteristics vary over a normal operating range. The signal fed back on line 98 from the transducer 22 is derived over a compensation network 100 which provides additional frequency selectivity and phase shift stability. The variable gain amplifier 94 is used to establish the loop gain during initial calibration of the filter circuits 90 and 92, and thereafter remains fixed after the calibration is complete.

A power amplifier and transformer section 104 provides a maximum-driving voltage of about 380 volts RMS with a maximum current of about 10 mA RMS. A gain control network 106 provides a stable voltage signal output by comparing the driving voltage on line 110 with a command voltage reference level on line 112 provided by a command signal derived from a control console in accordance with the power level desired by the surgeon using the phaco probe 20, and then compensating for any differences by adjusting the gain of the power amplifier of section 104.

In operation, the closed loop portion 84 of the driving circuit 80 attempts to compensate for changes in the resonant frequency of the transducer and/or phaco probe. This changing resonance is due to a variety of local factors which materially influence the ultrasonic transducer 22 and/or probe 20. Possible factors which can vary while the probe 20 is being used include the following: (1) the degree of compression of the transducer 22 on account of changing thermal or mechanical conditions; (2) the variations in the density or other properties in the fluid and/or debris being sucked by the vacuum through the channel 72 of probe 20; (3) the mechanical pressure brought to bear against the tip of the needle 28; (4) the quality of the coupling between the resonator 26 and needle 28; and (5) changes in the efficiency of the transmission of ultrasonic energy between the crystals 32 and 34 and the resonator 26 due to minute air gaps or mechanical deformations which may occur over time. One advantage of the driving circuit 80 of FIG. 2 is that the closed loop section 84 continually attempts to make the frequency of the input signal applied to the probe 20 match the changing resonant frequency of the transducer 22 and probe 20 combination during use. Although the Q of the resonator 26 itself is very sharp, on the order of 1,000 to 2,000, and its bandwidth is very narrow, on the order of 15 to 30 Hz, the Q of the overall probe/transducer combination is much less, on the order of 40 to 100, which results in a much wider bandwidth, on the order of 300 to 750 Hz. Thus even with the closed loop system, it has proved difficult under actual conditions to achieve consistently the desired match up between the frequency of the input signal to section 104 and the actual instantaneous resonant frequency of the transducer/probe combination.

As is well known, it is beneficial, in terms of operating efficiency, to provide a driving signal to an ultrasonic transducer at its nominal resonant frequency. It has also been determined that when there is a slight mis-match between the frequency of the input signal and the natural resonant frequency of the transducer/probe combination, the stroke length of the needle is varied even as the command voltage supplied on line 112 from the console remains constant. At times, this mis-match of frequencies can result in a noticeable change in the ability of the oscillating needle 28 to perform its function, such as shattering the cataract within the eye. An operating surgeon who notices this change in performance will tend to compensate for such variations by either increasing or decreasing the strength of the command signal as needed. However, it would be quite advantageous to have a phaco probe driving circuit which is capable of maintaining the stroke length substantially constant even as the resonant frequency of the transducer/probe combination changes on account of one or more of the aforementioned five factors so that the surgeon would not have to compensate manually for such changes.

In light of the foregoing observation, it is a first object of the present invention to provide a system and method for automatically determining the resonant frequency of an ultrasonic transducer. A related object of the present invention is to provide a method for automatically checking whether an ultrasonic instrument is in proper operating condition.

A second important object of the present invention is to provide a driving system for an ultrasonic transducer/phaco probe combination which automatically maintains the needle stroke length constant for a constant input command from the user. Another related object of the present invention is to provide a method of driving an ultrasonic transducer of an ophthalmic surgical instrument by holding electrical power consumed by the transducer substantially constant for a desired level of power consumption through the use of closed loop feedback control.

SUMMARY OF THE INVENTION

In light of the foregoing objects, there is provided, according to a first aspect of the present invention, a method for automatically determining the resonant frequency of a surgical instrument powered by an ultrasonic transducer. This method comprises the steps of: (a) providing an alternating current electric driving signal during a substantially constant voltage level to drive the ultrasonic transducer at any desired one of a number of frequencies within a given range of frequencies; (b) monitoring the electrical power consumed by the probe at different frequencies within the range of frequencies; (c) selecting an apparent resonant frequency within the range of frequencies by determining which frequency, out of those frequencies which were monitored, had the greatest electrical power from the driving signal consumed by the probe; (d) comparing the amount of power consumed at the apparent resonant frequency with amounts of power consumed by the probe at a first frequency below the apparent resonant frequency and at a second frequency above the apparent resonant frequency; and (e) deciding whether the apparent resonant frequency is the dominant resonant frequency of the probe at least in part based upon the results of the comparisons performed in step (d).

According to a second aspect of the present invention, there is provided a method for checking if an ultrasonic transducer in a surgical instrument is in proper operating condition. This method comprises the steps of: (a) providing an alternating current electric driving signal to the transducer in order to drive the transducer at any desired one of a number of frequencies within a given range of frequencies; (b) changing the frequency of the driving signal such that the driving signal operates at plurality of different frequencies spanning the range of frequencies; (c) monitoring the electrical power consumed by the probe at different frequencies within the range of frequencies; (d) finding an apparent resonant frequency within the range of frequencies by locating at least one frequency at which a maximum amount of electrical power from the driving signal is consumed by the probe; (e) determining, for a first band of frequencies above the apparent resonant frequency and within the range of frequencies, whether the amount of power consumed by the probe decreases monotonically within increasing frequency; (f) determining, for a second band of frequencies below the apparent resonant frequency and within the range of frequencies, whether the amount of power consumed by the probe decreases monotonically within the decreasing frequency; (g) deciding whether the probe is in proper operating condition by at least in part requiring that steps (e) and (f) each indicate that the power consumed by the probe monotonically decrease within the first and second bands of frequencies from the apparent resonant frequency, and wherein steps (c) through (g) are performed at least substantially automatically by electronic control means.

According to a third aspect of the present invention, there is provided a method for driving an ultrasonic transducer of an ophthalmic surgical instrument by holding the electrical power consumed by the transducer substantially constant at a desired level of power consumption by the use of closed loop feedback control. This method comprises the steps of: (a) generating an electrical signal oscillating at a desired ultrasonic frequency; (b) amplifying the oscillating electrical signal; (c) applying the amplified electrical signal to an ultrasonic transducer; (d) monitoring how much electrical power of the amplified electrical signal is consumed by the ultrasonic transducer; (e) comparing how much electrical power of the amplified electrical signal is being consumed against the desired level of power consumption; and (f) automatically adjusting the power level of amplified signal to maintain the consumed electrical power substantially equal to the desired power level.

According to a fourth aspect of the present invention, there is provided an electronic control system for determining the dominant resonant frequency of an ophthalmic surgical instrument containing an ultrasonic transducer and for thereafter driving the transducer at its dominant resonant frequency. This control system comprises: (a) means for producing a variable frequency alternating current ("AC") electrical signal to power the ultrasonic transducer; (b) means for monitoring electrical power consumed by the transducer from the AC electrical signal at any frequency of interest within a given range of frequencies; (c) means for determining at which frequency within the range of frequencies is the dominant resonant frequency under test conditions; (d) means for automatically commanding means (a) to produce its AC electrical signal at the determined dominant resonant frequency and at a desired level of power specified by a desired power command signal; and (e) automatic closed loop feedback control means, responsive to the means for monitoring, for adjusting the power of the AC electrical signal produced by means (a), such that a substantially constant level of power is consumed by the ultrasonic transducer substantially independently of changing conditions experienced by the probe when the desired level of power remains constant.

According to a fifth aspect of the present invention, there is provided an apparatus for automatically determining the resonant frequency of an ultrasonic transducer along the lines outlined in the first aspect of the present invention above.

According to a sixth aspect of the present invention, there is provided an apparatus for driving an ultrasonic transducer of an ophthalmic surgical instrument by regulating the electrical input power provided to the instrument. The apparatus comprises: (a) means for producing a first low power electrical signal having a first characteristic proportional to a desired power level; (b) means, adjustable under control of at least one feedback error signal, for amplifying the first low power electrical signal to produce a higher power electrical signal oscillating at a selected ultrasonic frequency; and (c) automatic closed loop feedback control means for producing at least one feedback error signal to adjust the level of amplification of the means for amplifying such that a substantially constant level of power is consumed when the desired power level remains constant.

The conceptual basis for the present invention is the belief that the electrical power consumption of an acoustic resonant transducer operating in a fundamental vibration mode is directly correlated to the vibration amplitude of the transducer. From a practical view point, a given population of acoustic transducers will have differing resonant frequencies and impedances. Therefore, one goal of the methods and control system of the present invention is to level out the performance of these transducers devices as measured by vibration amplitude. Since the acoustic resonator, for example the type shown in FIG. 1, may be used to mechanically drive a hollow phaco needle, the excursion of the needle tip, that is the cyclical stroke length, may be used to measure the performance of the entire phaco probe.

Previous phacoemulsification probe drive systems have used a variety of constant voltage or constant current circuit schemes. For example, the FIG. 2 phaco drive circuit described above used a constant voltage oscillator structure, where the availability of a drive signal depends directly on the compatibility between the probe's impedance characteristics and the probe's electrical interactions with both the amplifier output circuit and the feedback network. Accordingly, it is necessary to match the characteristics of the probe to be driven quite closely to the characteristics of the amplifier output circuit and feedback network.

In contrast the phaco drive system of the present invention operates in a constant power, direct drive mode. There is always a drive signal available. Further, the frequency of this drive signal is fixed based upon results of successfully completing a calibration routine. This routine or method is designed to find the fundamental resonant frequency of the phaco probe, and to ensure the compatibility between the probe power spectral characteristics and the driving circuit of the present invention.

These and other objects, advantages and aspects of the methods and drive system of the present invention may be further understood by referring to the detailed description, accompanying figures and dependent claims.

BRIEF DESCRIPTION OF THE DRAWINGS

The drawings form an integral part of the description of the preferred embodiments and are to be read in conjunction therewith. Like reference numerals designate the same or similar components or features in the various Figures, where.

DETAILED DESCRIPTION OF PREFERRED EMBODIMENTS

Figure 3:
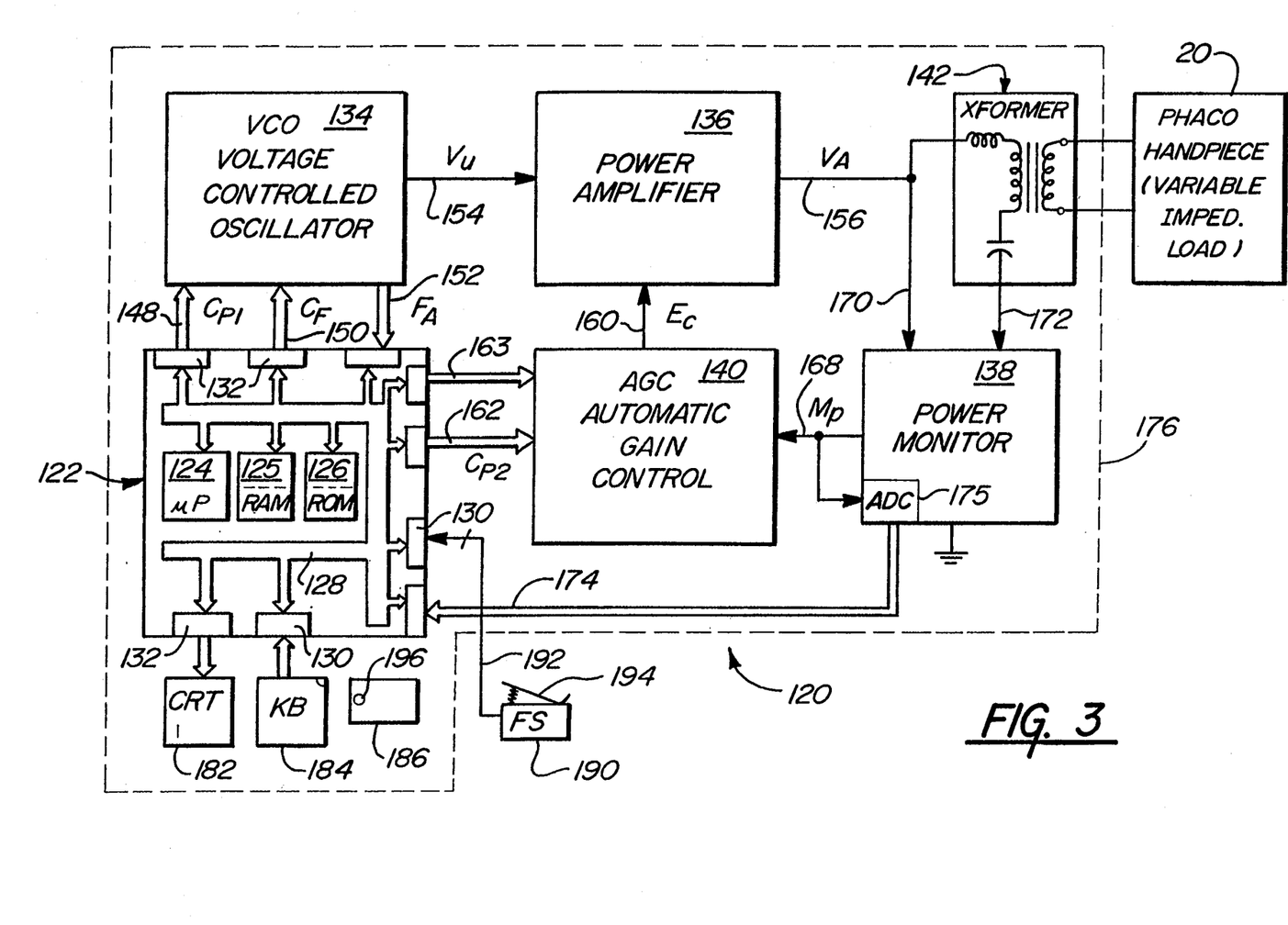
FIG. 3 is a simplified block diagram of the electronic control system of the present invention for calibrating and driving an ultrasonic transducer used in a phaco handpiece of the general type shown in FIG. 1.

FIG. 3 shows a simplified block diagram of the electronic control system 120 for determining the dominant resonant frequency of and for driving a phaco handpiece. The control system 120 includes: a microcomputer 122 having a processor 124, volatile (RAM) memory 125, nonvolatile (ROM) memory 126, and a control/address/data bus 128 communicating in conventional fashion with input ports 130 and output ports 132 and other portions of microcomputer 122; a voltage controlled oscillator ("VCO") section 134; a power amplifier section 136; a power monitor section 138; and an automatic gain control ("AGC") section 140. The control system 120 may also include a transformer section 142 for stepping up the voltage of the power drive signal delivered from the power amplifier 136 to the phaco handpiece 20. The microcomputer 122 provides a first desired power command signal ($C_{p1}$) on signal path 148. frequency command signal ($C_F$) on path 150 to the VCO section 134, and may optionally receive back an actual frequency signal ($F_A$) on signal path 152.

VCO section 134 provides to signal path 154 an unamplified sinusoidal signal ($V_U$) at the desired frequency whose amplitude is proportional to the desired power level specified by signal $C_{p1}$. This signal is amplified by power amplifier section 136, and which produces an amplified sinusoidal power signal ($V_A$) on line 156 which is supplied to the transformer section 142 and also to the power monitor section 138. Power amp section 136 also receives an error correction signal ($E_C$) on line 160 from AGC section 140. AGC section 140 receives a second desired power level command signal ($C_{P2}$) on path 162, and a control signal on path 163 from microcomputer 122, and receives a monitored power level signal ($M_P$) on line 168 from power monitor section 138. The power monitor section monitors the voltage and current of the amplified power signal supplied on line 156 via signal paths 170 and 172 respectively. The monitored power level signal is also provided to the microcomputer 122 via signal path 174 via analog-to-digital converter ("ADC") 175.

All of the foregoing equipment of control system 120 may be located in one control console indicated by dashed lines 176, if desired. The control console 176 may also include, if desired, a CRT or other information display panel 182, a key pad 184 and/or other operator actuated switches represented by block 186. In order to practice the present invention, it is not essential to use a microcomputer, since as should be appreciated by those skilled in the art, a hard-wired electronic control system may be used to realize the advantages of the present invention. Aforementioned U.S. patent application Ser. No. 428,232 describes in greater detail one possible implementation for the microcomputer-based surgical control console 176 which includes a CRT 182 and key pad 184 and which has been used to construct and operate prototypes of the electronic control system of the present invention. Aforementioned U.S. patent application Ser. No. 06/928,170 describes the Storz DAISY microcomputer-based control console which is another implementation for a console for use with the present invention. A microcomputer similar to either one of the microcomputers described in the two aforementioned patent applications may be utilized with the present invention. Each of these microcomputer systems displays menus and messages on the CRT 182 and allows the operator (who may be either the surgeon or the surgeon's assistant) to select desired functions relating to use of the phaco handpiece 20, such as irrigation and aspiration, which are well known. These additional functions do not constitute part of the present invention, and thus will not be described here.

The selection of the desired level of power for the phaco probe 22, as well as the control of irrigation and aspiration, is normally accomplished via a foot switch assembly 190 connected to the microcomputer 122 by appropriate controls signals via signal path 192. By stepping on the spring-biased foot pedal 194 of foot switch assembly 190, the ophthalmic surgeon indicates to the microcomputer 122 the desired level of phaco power. However, if desired, the surgeon may also select the desired level of power through the use of a potentiometer 196 in the control block 186, or by selecting a desired value in the key pad 184. In either case, the selected level of phaco power may be displayed on information display 182. Also, if desired a fixed level of power maybe employed by the surgeon, by holding the foot pedal 194 steady at one position, or by selecting a set value through the key pad 184 or potentiometer 196. These techniques for selecting desired power levels in surgical procedures involving the use of a phaco handpiece are all well known.

The block diagram of the FIG. 3 control system 120 shows two distinct control loops. The outer loop begins and ends with the microcomputer 122 and includes sections 136, 138 and 142. This loop is active only during the phaco calibration procedure which will be described in greater detail later, but may briefly be described now as follows.

The processor 124 sends a series of signals representing different frequency commands to the VCO section 134, where the commands are each converted to a voltage level representing the desired frequency. A sine wave signal $V_U$ is output by VCO section 134 on line 154, and is amplified by amplifier section 136, and presented via line 156 to the transformer section 142 which applies it to the phaco handpiece 20. The error correction command signal on line 160 applied to the power amplifier section 136 is a fixed value on account of the control signal on path 163 to the AGC section 140 by the processor 124. The power monitor 138 samples the voltages being applied to the transformer/probe via line 170 and also samples the current returning from the transformer section 142 via line 172. From these samples, the electrical power is computed in power monitor section 138, and an analog voltage signal ($M_P$) having an amplitude corresponding to the monitored power level is produced and output by section 138 on line 168.

The value of this analog voltage $M_P$ is also delivered to the microcomputer 122, via ADC 175 which converts it to 12 bit digital data and transmits it back to the processor 122 as the "load power" value, that is the electrical power consumed by the probe 20. The processor 124 fills a table in memory 125 with ordered pairs consisting of signal frequencies and load power information. Several tests are performed on this data, which will be described later below, which ensure a minimum compliance of the curve representing the acquired data against standard curve for an ideal ultrasonic transducer/probe combination. Certain variances from the standard curve indicate specific types of failure conditions existing in the phaco handpiece 20, such as open or short circuits, missing or loose needles, and excessively damped transducers. These tests will also fail if the wrong transducer type is connected to the transformer section 142.

If the initial calibration procedure is successful, the processor 124 will store the frequency at which the load power was at a maximum. That single frequency will then be used when driving the phaco handpiece 20 until such time as the next phaco calibration sequence is performed. After calibration, the outer control loop just described is opened, and the inner control loop is engaged.

The inner control loop uses the automatic gain control section 140 as well as sections 136, 138 and 142. When the inner control loop is to be engaged, an appropriate control signal is provided on path 163, which enables an automatically determined error correction signal on line 160 to be provided to the power amplifier section 136.

The operation of the automatic gain control section 140 may be summarized as follows. When the processor 124 commands a specific percent power level via signal $C_{P2}$ on path 162, an analog reference voltage is generated internally with the AGC section 140. The voltage representing load power on line 168 is compared to this reference voltage and the difference is integrated in the hardware of the AGC section 140. The output of an internal integrator circuit is provided as the error correction signal $E_C$ on line 160, and drives the gate of a field effect transistor ("FET") located in power amplifier section 136. The channel resistance of this FET provides a shunt path to ground for the desired power level command signal $V_U$ provided on line 154. The larger the channel resistance of the FET, the stronger the power signal provided to drive the probe 20. The result of the operation of the closed loop is that the amplitude of the power signal on line 156 is constantly changing to match the changing impedance characteristics of the probe 20.

Figure 4:
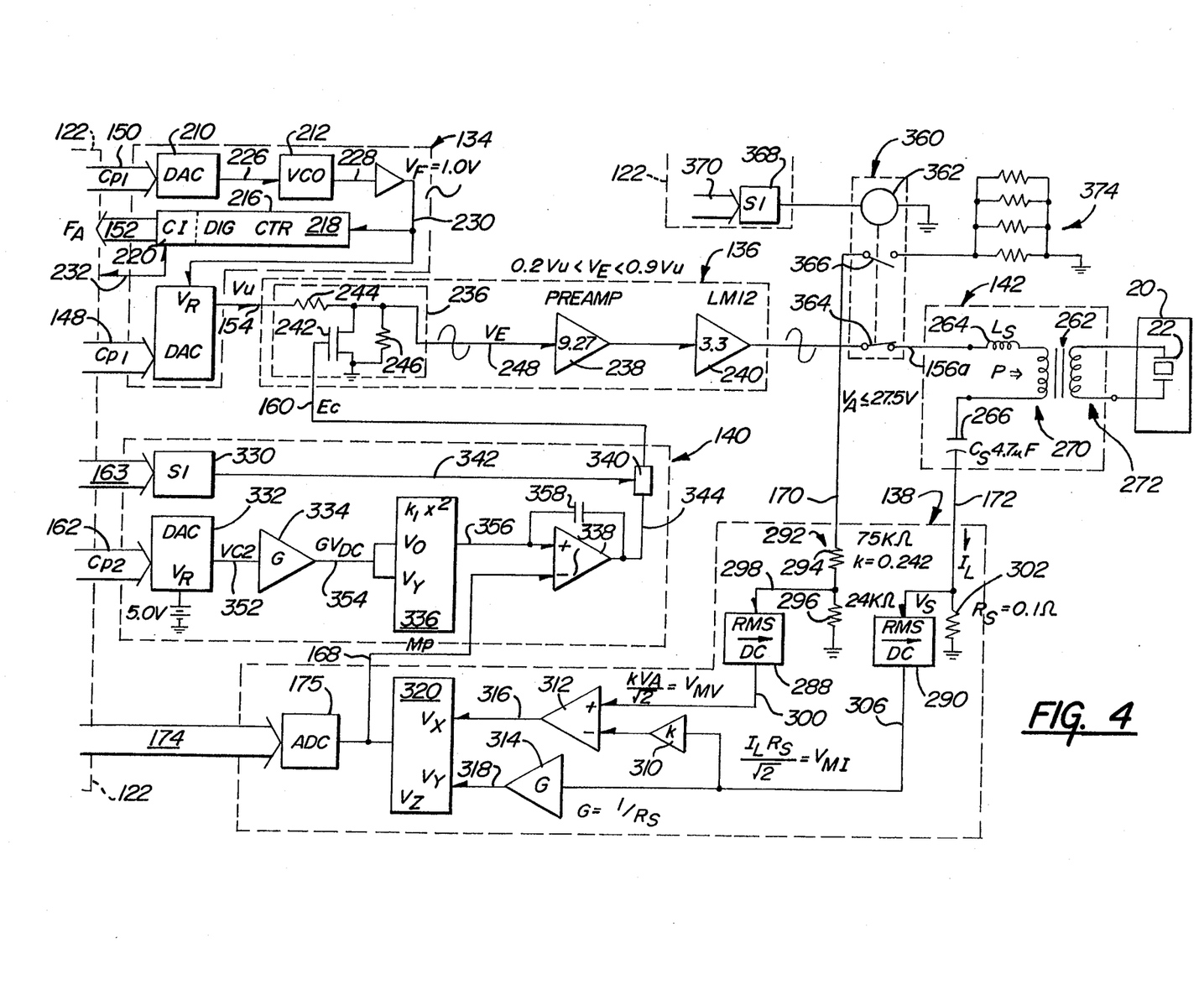
FIG. 4 is a detailed block diagram of the FIG. 3 control system showing the various functional components of the electronic hardware thereof.

FIG. 4 shows a detailed block diagram of the control system 120 shown in FIG. 3, except for the microcomputer system 122. In particular, FIG. 4 shows all of the functional hardware components which constitute part of the driving circuitry of control system 120. The major blocks shown in FIG. 3 are shown in dashed lines in FIG. 4 to facilitate comparison between FIGS. 3 and 4. The components within the various blocks will be discussed, followed by an explanation of the interaction of the various sections.

VCO section 134 includes a digital-to-analog converter ("DAC") 210, a voltage controlled oscillator 212, pre-amplifier 214, a frequency counter 216 including a digital counter section 218 and control interface 220 and a second DAC 222. The first DAC 210 receives the frequency command signal on path 152 in digital form and converts it to a corresponding analog voltage on line 226 which inputs it into the oscillator 212. VCO 212 produces a sinusoidal output signal having a frequency corresponding to the applied input voltage. The design of the voltage controlled oscillator 212 is conventional, and may be designed to produce an output signal in a selected range of frequencies. In the preferred embodiment, the VCO 212 produces 35 kilohertz at the minimum input voltage and 21 kilohertz at the maximum input voltage $V_{CC}$. DAC 210 and DAC 222 preferably have 12-bit resolution for 4,096 different possible output values. Pre-amplifier 214 strengthens and smoothes out the sinusoidal signal on line 228 to produce a fixed amplitude voltage signal ($V_F$) on line 230. Signal $V_F$ is fed to the input of frequency counter 216 and to the voltage reference terminal of DAC 222.

Frequency counter 216 is used to check the output frequency of the VCO 212 in response to known values input to DAC 210 by signal path 152. Control signals delivered on path 232 from microcomputer 122 to the control interface 220 tell counter 216 when to start and stop counting the cycles of signal $V_F$, and when to transfer the accumulated count to microcomputer 122. In this manner, the performance of DAC 210 and VCO 212 can be checked by microcomputer 122 to ensure both are operating properly.

Signal $V_F$ serves as the reference voltage for the second DAC 222, which receives as its input signal the first desired power level command $C_{P1}$ on path 148. Accordingly, the signal $V_U$ output on line 154 by DAC 222 is the sinusoidal signal $V_F$ modulated by the value of the input signal received by DAC 222. Thus the amplitude of signal $V_U$ is directly proportional to the value of the digital signal $C_{p1}$ on path 148.

Power amplifier section 136 includes three stages: a FET attenuator 236, a preamplifier 238 having a fixed gain of 9.27, and a power amplifier 240 having a fixed gain of 3.3. The FET attenuator 236 includes a FET 242 and resistors 244 and 246 which output the signal $V_E$ on line 248. The FET attenuator is of standard design and operates as a voltage controlled resistor with the signal $E_C$ supplied on line 160 being the control voltage. When the voltage $E_C$ is high, the channel resistance of FET 242 is very high, and therefore a maximum amount of power of the signal $V_U$ passes through to line 248, with the reduction amplitude being determined by the voltage divider network formed by resistances 244 and 246. The input impedance of preamp 238 is high in comparison to the values of resistors 244 and 246, and thus can be ignored. As the amplitude of the signal $E_C$ decreases, FET 242 begins to turn on correspondingly, thus reducing the amplitude of signal $V_E$ on line 248. FET 242 and resistor 244 are chosen so that when the FET is fully on, $V_E = 0.2 V_U$, and when FET 242 is fully off, $V_E =$ about $0.9 V_U$. Power amplifier section 136 thus produces as its output on line 156 signal $V_A$ which can vary from zero volts up to about 27.5 volts, depending upon the level of input signal $V_U$ delivered on line 154.

Transformer section 142 steps up the voltage of signal $V_A$ by about 30 times. Section 142 includes a conventional power step up transformer 262 having a certain parasitic inductance $L_S$ symbolically represented by inductor 264 and a fixed capacitor 266 sized at a nominal frequency of 30 KHz to cancel out the effects of parasitic inductance $L_S$. Thus the primary circuit 270 of section 142 includes the well-known RLC series resonant circuit used to drive ultrasonic transducers. The connection of the secondary 272 of section 142 to the probe 20 is conventional and need not be discussed here.

Power monitor section 138 includes: a first and second $AC_{RMS}$-to-DC voltage converters 288 and 290, voltage divider network 292 formed of resistors 294 and 296 with the divided voltage being picked off on line 298 and supplied as an input to converter 288. The constant "k" represents the attenuation provided by voltage divider network 292, where $k = R_{296}/(R_{292} + R_{296})$. Thus, converter 288 develops on line 300 an output signal $V_{MV} =$ to $1.414 kV_A$.

Section 138 receives on line 172 the actual load current $I_L$ being used in the primary 270 of transformer 262. Sense resistor 302 develops a sense voltage $V_S$ directly proportional to the magnitude of current $I_L$, which is delivered as an input to converter 290. Thus the output of converter 290 on line 306 is a voltage signal $V_{MI}$, where $V_{MI} = 1.414 I_L R_S$. The signal on line 306 is passed through amplifier 310 which multiplies it by the value "k" and then passes it to the negative input of difference amplifier 312 and to the fixed gain amplifier 314 which has a gain G, where $G = 1/R_S$.

The signal $V_{MW}$ is applied to the positive input of difference amplifier 312. The outputs of amplifiers 312 and 314 are delivered as inputs to multiplier 318 which produces the monitored power signal $M_P$ which is a voltage signal whose amplitude is proportional to the product of input signals 316 and 318 supplied to multiplier 320. The difference amplifier 312 is employed in order to subtract out from the signal $V_{MV}$ the effect of the voltage drop across sense resistor 302. Calculations show that the amount of power lost across resistor 302 represents well under 10% of the total power consumed by the probe 20, even under most low power conditions. Thus the amplifiers 310 and 312 could be omitted and the line 300 wired directly to the $V_X$ input of multiplier 320 if desired. However, for the sake of more accurate performance, the preferred embodiment includes amplifiers 310 and 312 as shown. The signal $M_P$ on line 168 is also supplied to 12-bit resolution ADC 175 which, as previously explained, outputs the digital value of the signal $M_P$ to microcomputer 122.

AGC section 140 includes signal interface 330, 12-bit resolution DAC 332, voltage amplifier 334 having a fixed gain G, multiplier 336, integrating difference amplifier 338 and analog switch 340, all connected as shown. Signal interface 330 conditions the control signal on line 163 from microcomputer 122 to produce the digital control signal 342. In one state, the signal on line 342 causes analog switch 340 to be nonconducting, thus blocking the output signal on line 344 from passing to line 160. In its other state, the control signal on line 342 causes analog switch 340 to be fully conducting, thus allowing the output signal of line 344 to pass freely to line 160. Those in the art will appreciate when analog switch 340 is rendered nonconducting by the signal on line 342, the AGC section 140 is effectively removed from the control system, as was described within the explanation of the calibration procedures above with respect to FIG. 3.

DAC 332 converts the digital $C_{P2}$ on path 163 to an analog value $V_{C2}$ on line 352. Signal $V_{C2}$ is multiplied by G in amplifier 334 and passed to both inputs of multiplier 336. The resulting output signal on line 356 of multiplier 336 is thus proportional to the square of the input signal presented on line 354. The motivation for using the multiplier 336 in the AGC section 140 is that it effectively increases the dynamic range of AGC section 140 which not sacrificing much if anything in the way of accuracy. In the preferred embodiment, the digital value $C_{P2}$ is proportional to the square root of the desired power level signal $C_{P1}$, whose value is proportional to desired level of power communicated by the surgeon to the microcomputer 122. If multiplier 336 were not used, then, the signal $C_{P2}$ would be directly proportional to the desired level of power, and the output of scaling amplifier 334 would be fed directly to the positive input of integrating difference amplifier 338. By providing the square root of the desired power signal as the digital value $C_{P2}$ on path 162, the AGC section is provided with greater sensitivity at lower values of desired power, which can be advantageous from a user's point of view.

Difference amplifier 338 includes a feedback capacitor 358 so that AGC circuit thus employs both proportional and integral, while still providing feedback control. As is well known, integral feedback control has the beneficial tendency under steady-state loop conditions to drive the absolute errors in a closed loop feedback system to zero. In the preferred embodiment, the capacitor 358 is sized to have an RC time constant of approximately 35 to 100 milliseconds with about 50 to 65 milliseconds being preferred, and the amplifier 338 preferably has a gain of about one.

When the inner loop is engaged, the control system 120 shown in FIG. 4 continuously provides a driving signal $V_A$ on line 156 whenever the desired power level signals $C_{P1}$ and $C_{P2}$ are non zero. Further, the frequency of the driving signal when the probe 20 is in use is always set at the dominant resonant frequency of the transducer/probe combination, as determined by the calibration procedure, which will be more fully explained shortly. The effect of changes in the actual instantaneous resonant frequency of the combination of the probe 20 and its ultrasonic transducer 22 is compensated for by the error signal $E_C$ produced by the AGC section 140, which automatically adjusts the effective gain of power amplifier section 136 as needed. As can be seen from the foregoing discussion of power monitor section 136 and AGC section 140, the actual electrical power consumed by the probe/transducer combination is compared against the desired power level to obtain the correction signal. For stability and in order to eliminate long-term offset errors in the closed loop system, difference amplifier 338 integrates the error signal on its output 344.

Those in the art should appreciate that the hardware shown in FIG. 4 does not monitor or otherwise take into account the relative phase differences which may exist between the phases of voltage signal $V_A$ and current signal $I_L$. Thus, the FIG. 4 embodiment actually monitors apparent electrical power consumed by the probe/transducer combination, rather than true (or real) electrical power consumed. However, in the aggregate, the phase differences are usually small enough to be insignificant, and therefore may be safely ignored, or are relatively constant over the range of changing resonant frequencies for any given probe, and thus are also transparent to the user of the control system 120. Thus, the preferred embodiment of the present invention does not monitor this phase difference. However those skilled in the art will appreciate that, if desired, the true electrical power consumed by the probe/transducer combination could be monitored by providing an additional circuit to take into account the difference between apparent power and actual power resulting from phase shifts between signals $V_A$ and $I_L$.

FIG. 4 also shows a power relay 360 having a coil 362, normally closed contact 364 and normally open contact 366. The relay coil is energized when a signal interface circuit 368 receives a control signal 370 from microcomputer 122 directing that the relay be turned on. When coil 362 is de-energized, normally closed contact 364 is closed, thus allowing the signal on line 156 to pass through to line 156a and onto transformer section 142. When coil 362 is energized, normally closed contact 364 opens, and normally open contact 366 closes, which directs the power of amplifier 240 from the signal on line 156 to a 60 watt load resistor bank 374 connected to ground. The use of relay 360 and dummy load resistance 374 allows the microcomputer 122 to verify that the circuitry in FIG. 4 is operating properly. In particular, before surgical use of the control system 120, microcomputer 122 can verify a proper operation of the control system 120 by energizing relay 362 and applying known power command signals to the control system 120, and checking for expected performance (within an acceptable tolerance). In the preferred embodiment of the present invention, the dummy load 374 simulates an ultrasonic transducer 22 which has an impedance of 8100 ohms.

It is known in the art to provide at least two modes of operation for phaco driving circuits, namely the "fixed phaco" mode and the "linear phaco" mode. In the Storz DAISY console, these modes operate as follows. In the fixed phaco mode, phacoemulsification power and aspiration are determined by the console controls (i.e., the keyboard 184 and/or potentiometer 196) and the foot switch assembly 190 controls the application of irrigation, aspiration and phacoemulsification. In the linear phaco mode, phacoemulsification power is controlled by the foot switch, and the aspiration is determined by the console controls. Either mode of phaco operation can be readily supported by the electronic control system of the present invention.

In the fixed phaco mode, the desired level of power control in the Storz DAISY console can be adjusted from about 50% to 100% in fixed increments, such as 5%. The microcomputer 122 also can be readily programmed to drive the phaco probe in a pulsating mode rather than continuous mode if desired. In the pulsating mode, a pulse rate control value can be adjusted, for example, from 0 to 20 pulses per second in increments of one pulse per second. When the pulse rate control is made operative, the desired power level and the pulse rate control work together to determine the aggregate phacoemulsification power applied via the probe 20 to the patient's eye. In the Storz DAISY console, the pulse rate control is not used to adjust the desired phacoemulsification power level. Instead, the pulse rate control adjusts the number of cycles of phacoemulsification power that occur during a given time. The purpose of the pulsating mode is to allow the irrigation/aspiration functions to periodically clear the eye of material during a surgical procedure using phacoemulsification. This is believed to help prevent the disintegrated cataract fragments still in the eye from obstructing the surgeon's vision by more efficiently removing same. In the DAISY console, all these parameters associated with the fixed, linear, continuous and pulsating modes of phaco operation are selectable via the keyboard 184 or the set 186 of control knobs, and the selected settings are displayed on the CRT 182. The electronic control system 120 of the present invention can also be readily used to support these same types of functions. Further description of these functions need not be given here since they are well-known and do not constitute part: of the present invention.

Figure 5:
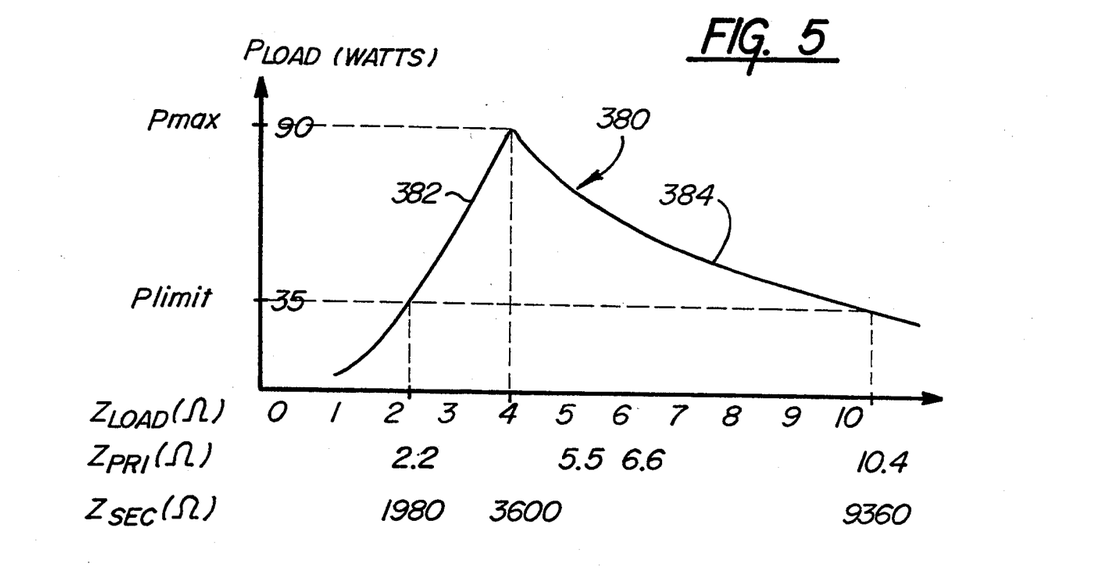
FIG. 5 is a graph illustrating the power transfer characteristics of the power amplifier section of the FIG. 3 control system, and how they can be utilized to apply a constant power limit to phaco probes having wide range of input impedances.

FIG. 5 shows typical power transfer characteristics of an electronic amplifier or circuit, such as power amplifier section 136, designed to have an output impedance of 4 ohms. FIG. 5 shows a graph of the power consumed by various resistive loads when using a ±30 volt (peak) AC power source and a maximum signal voltage of ±27 volts (peak). As expected, the curve 380 has a portion 382 which rises as the load impedance increases from 1 ohms to 4 ohms, and a portion 384 which decreases as the load impedance changes from 4 ohms to 10 ohms. In order to make the power amplifier section 136 operate effectively over a relatively wide range of impedances from about 2 ohms to about 10 ohms, a power limit of 35 watts is imposed by design upon the performance of amplifier section 136, even though at 4.0 ohms it could, if unrestricted, deliver a maximum power of 90 watts. Limiting a power amplifier to a fixed upper power limit, such as 35 watts, is a well-known design technique for audio power amplifiers, and need not be described further here, other than to note that such techniques are used in power amplifier section 136 of the present invention.

In FIG. 5, the second and third sets of numbers below the horizontal axis are labeled $Z_{PRI}$ and $Z_{SEC}$, and represent the primary and secondary impedances of the 30:1 step-up transformer 262.

Figure 6:
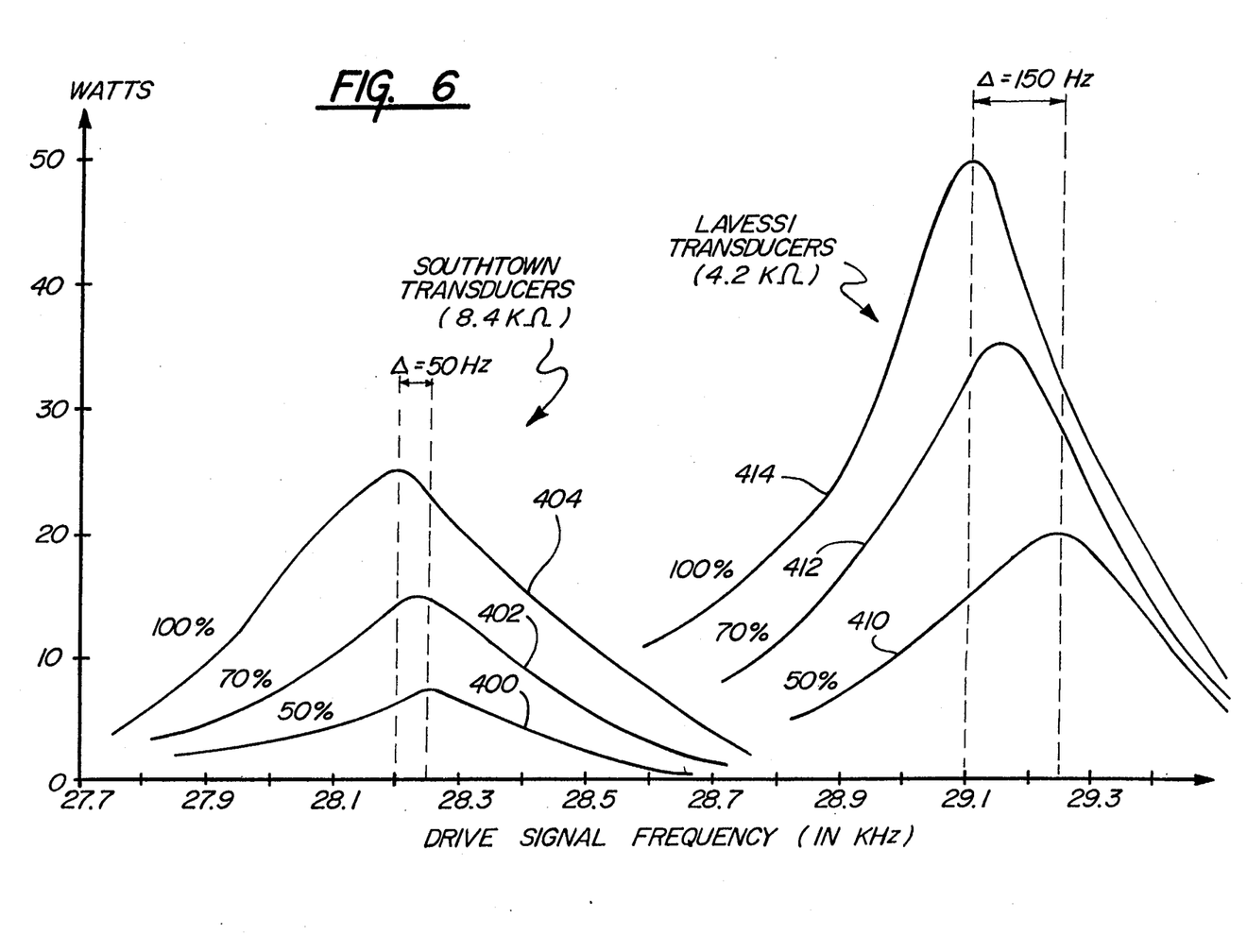
FIG. 6 are two sets of graphs showing the output power versus input frequency response characteristics or curves obtained from two different types of phaco probes driven at 50, 70 and 100 percent power levels by a 35 watt power amplifier set up to drive a 6 kilo-ohm load.
Figure 7:
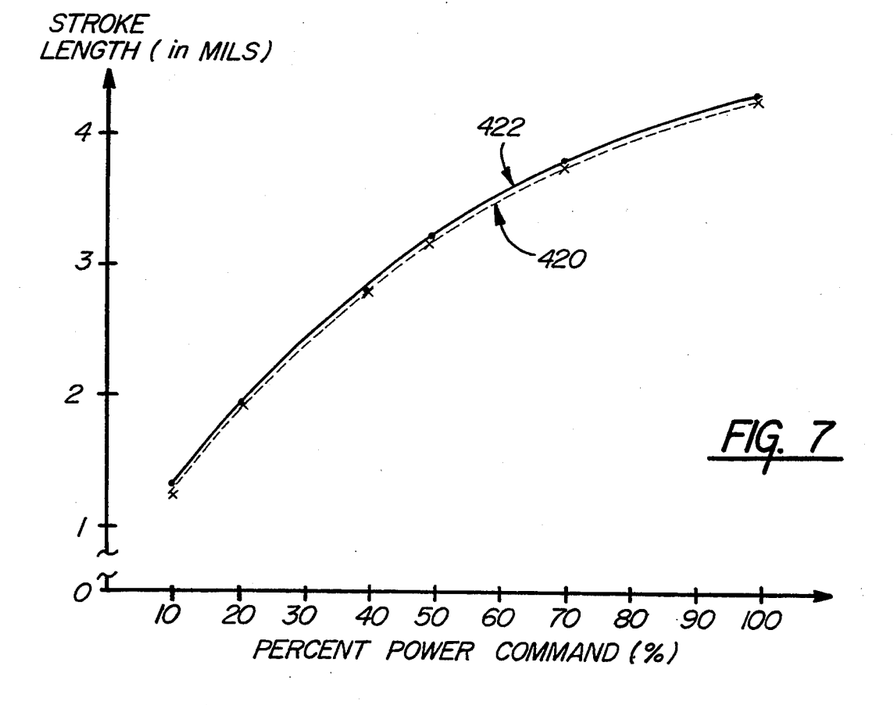
FIG. 7 shows the output stroke versus percent power command characteristics of the phaco probes used to generate the FIG. 6 graphs when such probes are driven by the electronic control system of the present invention.

FIGS. 6 and 7 help illustrate graphically the validity of the design concept of the present invention. FIG. 6 shows the variance in electrical power consumption between two distinct families of ultrasonic transducers with the families having very different resonant frequencies. Curves 400, 402 and 404 represent the average power consumed by four transducers in one family from one commercial supplier (Southtown Machine Co. of St. Louis, Mo.) at power levels of 50%, 70% and 100% (where 100% =35 watts). This first family of transducers has a nominal impedance of 8.4 kilo-ohms and a resonant frequency of about 28.2 KHz. Curves 410, 412 and 414 represent the average power consumed by eight transducers from another commercial supplier (Lavezzi Precision, Inc. of Elmhurst, Ill.) at power settings of 50%, 70% and 100%. This second family of transducers had a nominal impedance rating of 4.2 kilo-ohms, and a resonant frequency in the range of 29.1 to 29.25 KHz. Thus, FIG. 6 shows that there is a tremendous variance in resonant frequencies and in electrical power consumption between two distinct populations of ultrasonic transducers.

It would be very desirable to have a single phaco probe drive system that would operate phaco probes using transducers from either family successfully and without much if any variance in probe performance. The probe driving circuitry of the present invention does this. The differences between the peak power consumption and the resonant frequencies of the two populations of transducers is of no major concern. In order to have both families of transducers being successfully driven by the electronic control system of the present invention, then only the power amplifier selection and frequency band widths of the various sections of the control system need be selected and designed to operate over the desired range of frequencies. As may be seen from FIG. 5, the power amplifier section 136 is easily made to operate over a primary impedance range of 2.2 ohms through 10.4 ohms by simply limiting the maximum power produced by amplifier section 136 to an appropriate fraction of its peak power, such as about 35 percent as shown in FIG. 5.

In prior art driving systems for phaco probes, the difference in peak electrical power consumption between transducers populations is a major concern, particularly for drive systems employing a constant voltage strategy. In fact, the graphs in FIG. 6 were generated from a nearly constant voltage drive source. The input voltage to the power amplifier driving the RLC transformer section was constant, but there was no compensation circuitry to maintain the output voltage constant. So as the load impedance varied, so did the output voltage of the power amplifier because of the voltage divider relationship between the load impedance and source (output) impedance. This relationship is largely responsible for the power transfer characteristics shown in FIG. 6.

FIG. 7 demonstrates the similarities between transducer performance of the two populations of transducers shown in FIG. 6 when driven by the phaco drive system of the present invention shown in FIG. 4. Since the effective impedance of the two transducer populations, namely 4.2 kilo-ohms and 8.4 kilo-ohms, are within the constant power drive range of the power amplifier section 136 and step-up transformer sections, (which range extends from about 2 kilo-ohms to about 9.3 kilo-ohms), there is no problem with maintaining constant power at the output of the transformer secondary. Thus, as shown in FIG. 7, the performance of probe 20 using a transducer 22 from either family is remarkably similar.

Another advantage of the present invention is that, even if the impedance characteristics of the transducer/probe drift outside of the constant power amplifier range, so that constant power cannot be strictly maintained, the drive system of the present invention will nevertheless strive to deliver a proper amount of power to the transducer. This is far superior to the total loss of power experienced with some phaco drive systems under such conditions.

The FIG. 7 graph shows the close correlation between the results achieved by the electronic control system 120 of the present invention when driving the two different families of transducers shown in FIG. 6. Dashed line 420 represents the actual stoke length (in mils) as a function of percent power command for those transducers having a nominal impedance of 8.4 kilo-ohms. Solid curve 422 represents the performance of those transducers having a nominal impedance of 4.2 kilo-ohms when driven by the control system of the present invention. As FIG. 7 graphically shows, the resulting performance of phaco probes using either type of transducer is nearly identical. The performance is also quite linear over the range from 10% power to 100% power. The slight nonlinearities in the curves 420 and 422 are believed due to saturation effects in the ultrasonic transducer due to power limitations. However, as a practical matter, these nonlinearities should be inconsequential to ophthalmic surgeons, since the surgeons are interested principally in consistency, repeatability and reasonable (not perfect) linearity, all of which characteristics are achieved by the drive system of the present invention.

Figure 8:
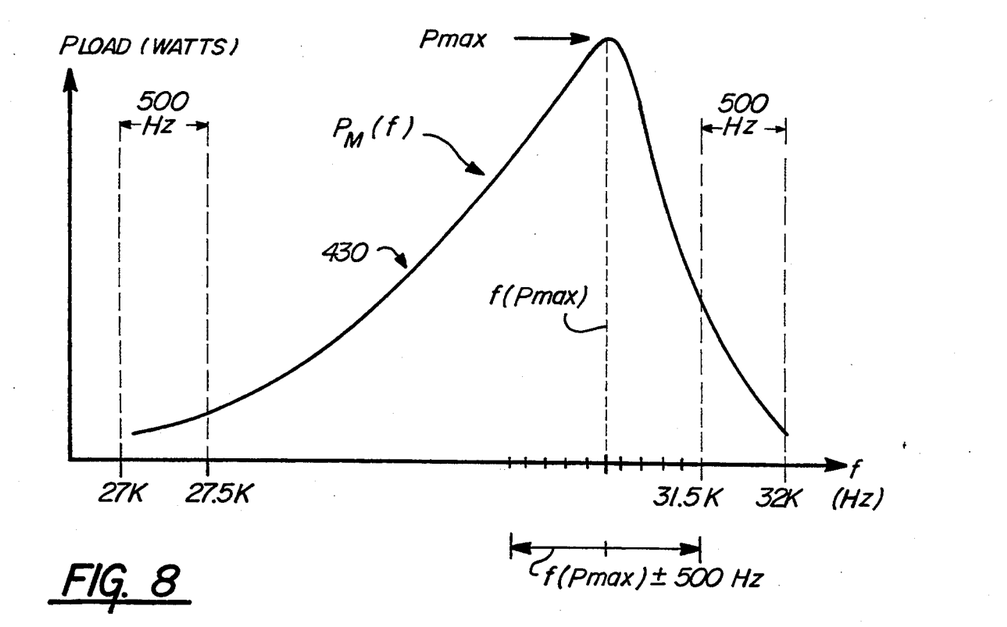
FIG. 8 is an annotated graph showing a prototypical output power versus input frequency curve for a phaco probe, which helps illustrate the calibration method of the present invention used to qualify phaco probes and determine their resonant frequency.

FIG. 8 shows a prototypical or standard curve of consumed power versus drive frequency of an ultrasonic transducer having a true or dominant resonant frequency of about 30 kilohertz. The shape of the curve is also representative of the consumed power curve for other ultrasonic transducers used in phaco probes which operate at different frequencies. In other words, if the power consumed curve for an ultrasonic transducer/probe combination (when assembled) resembles this curve within certain limits under known test conditions, then such evidence constitutes good proof that the tested transducer/probe combination is in proper operating condition and ready to be satisfactorily used by an ophthalmic surgeon. The determination of the resonant frequency of a given ultrasonic transducer/probe combination and the verification of proper operation of such combination constitutes two important and distinct aspects of the present invention. These aspects of the present invention are more fully explained below.

In order to simplify the following explanation, it is assumed that the range of normal frequencies of the transducers to be operated by the electronic drive system of the present invention conform to the families of curves shown in FIG. 6. Further, the power amplifier section characteristics are assumed to be as shown in FIG. 5.

The electrical power consumed by the transducer/probe combination to be tested is determined by monitoring the voltage applied to and current passing through the primary 270 of the RLC transformer section 142 (FIG. 3). The frequency at which peak power is consumed may be considered to be the dominant resonant frequency $F_{DR}$ for the transducer/probe under test. The calibration procedure tests the transducer/probe by operating the power amplifier at half power (i.e., about 17.5 watts), and while so doing, sweeping the command frequency $C_F$ from 26.5 kilohertz to 32.5 kilohertz at 100 Hz increments and recording the monitored power signal $P_M$ obtained. Then, the stored data is analyzed to see whether the resulting curve conforms to certain criteria set as minimum "pass" conditions for grading the transducer/probe performance as satisfactory. Four or five criteria maybe used, if desired, and each one used must be met. First, the maximum power consumed by the probe at the apparent resonant frequency $F_{AR}$ must be greater than or equal to a predetermined power level, such as 12 watts. Second, the frequency $F_{AR}$ must fall between 27 kilohertz and 31.5 kilohertz. Third, the half-power band for the transducer/probe must be less than or equal to 1,000 Hz. In other words, at 0.5 KHz above and at 0.5 KHz below the frequency $F_{AR}$, the power consumed by the transducer/probe must be less than or equal to one-half of the maximum power consumed ($F_{Pmax}$) at the frequency $F_{AR}$. The fourth criterion which must be satisfied is that the consumed power at each of a selected number of readings below and closest to the frequency $F_{AR}$, and each of the readings at a selected number of readings above the frequency $F_{AR}$ must monotonically decrease with increasing distance from $F_{AR}$. The selected number of readings is preferably five. A fifth criterion is also preferably employed. This criterion requires that all readings more than 500 Hz away from the frequency $F_{AR}$ be less than or equal to a predetermined fractional value of $P_{max}$, such as less than 50% of $P_{max}$.

The software used in microcomputer 122 which implements the calibration procedures mentioned above and operates control system 120 in the following manner (See FIGS. 3 and 4). During the initialization of the microcomputer 122, the VCO section 134 is interrogated to determine its response under minimum and maximum conditions in order to verify that it is operational and to determine its frequency response. The signal applied to the VCO is simply a DC voltage signal which varies from 0 to 5 volts, and which is produced by a DAC 210. Frequency counter 216 is used to determine the frequency of the output signal being produced by VCO 212. Frequency counter 216 is digitally interrogated by the microprocessor 124 as previously explained with respect to FIG. 4, in the following manner.

The minimum condition or zero volts signal on line 226 is represented by all zeros in the 12-bit word $C_F$ sent to DAC 210 and the frequency output produced by VCO 212 is then determined. Normally it is about 35 KHz. Then, the maximum condition, namely, all ones in the 12-bit word $C_F$ is sent to the DAC 210 and the output frequency of the VCO 212 in response thereto is counted and reported by the frequency counter 216. (The VCO 212 is assumed to have a linear response between the two values tested for.)

The calibration procedure employed to determine the dominant resonant frequency $F_{DR}$ of the transducer/probe combination has two phases, a "coarse" phase and a "fine" phase. The output of the power amplifier section 136 is run at a 50% level for all steps of the coarse phase and fine phase. During the coarse phase, the following steps take place. The desired frequency of the probe is assumed to be somewhere between 27.0 KHz and 31.5 KHz. To assure that appropriate readings are taken, the frequency of the VCO is swept from 26.5 KHz up to 32.0 KHz. During the coarse phase, the frequency is incremented by 100 Hz with each successive power reading taken. At each 100 Hz increment from 26.5 KHz to 32 KHz, the (apparent) electrical power consumed by the probe is read by the power monitor section 138 and stored in RAM 125 of microcomputer 122. At the end of this coarse sweep, one of these readings will be the highest and is designated $P_{max}$, and its associated frequency will be presumed the apparent resonant frequency $F_{AR}$.

Next, the frequency $F_{AR}$ is checked in several ways to determine whether it is a true or dominant resonant frequency, and whether the ultrasonic transducer within the probe appears to be working properly. First, the frequency peak is checked to make sure it is within 27.0 to 31.5 KHz. Second, the peak amplitude $P_{max}$ must be above a predetermined minimum, such as 12 watts. (This minimum will be a function of the power level applied to the probe during the coarse sweep, and will normally be some value such as 65 or 75 percent of the sweep power level.) Third, for the five closest readings to and below frequency $F_{AR}$, and the five closest readings to and above frequency $F_{AR}$, each consumed power level must monotonically decrease from $P_{max}$ with increasing distance from the frequency $F_{AR}$. Fourth, the lower and upper power half-bands must occur respectively within $F_{AR}-500$ Hz, and $F_{AR}+500$ Hz. That is to say, the power consumed at $F_{AR}-500$ Hz and at $F_{AR}+500$ Hz must be either less than or equal to one-half of the power level $P_{max}$ recorded at the frequency $F_{AR}$. Fifth, every power consumption reading taken above $F_{AR}$ plus 500 Hz, and below $F_{AR}$ minus 500 Hz must be less than or equal to a predetermined value, such as 50% of $P_{max}$. If all the foregoing conditions are satisfied, the software announces that the transducer probe combination just tested passed the coarse phase of the calibration procedure.

The fine phase of the calibration procedure occurs next. During this phase, the probe is swept again, this time from $F_{AR}$ minus 200 Hz through $F_{AR}$ plus 200 Hz at 5 Hz increments. This is done to determine more accurately $F_{DR}$, which is assumed to be the frequency at which the highest power consumed reading occurs during this fine sweep. Thereafter the transducer/probe combination is deemed ready to be used in surgical procedures and a message that had earlier been displayed upon the monitor 182 of the control console, such as "phaco calibration required", is cleared from the monitor. The control system 120 will then always drive that transducer/probe combination at the last $F_{DR}$ determined during the calibration procedure.

The VCO 212 is preferably operated in an open loop fashion, since it is not necessary to operate it in a closed loop fashion. In other words, when the processor 124 commands VCO section 134 to operate at a specific frequency, say 28.3 KHz, it does not check the frequency counter to determine that the reading is actually achieved. Instead, it is assumed that the DAC 210 converter and the VCO 212 do not drift during the short time that the ultrasonic transducer/probe is being used. Note that even if the frequency output by the VCO is off by several Hertz, this will not matter since the key is not that the value of $F_{DR}$ be known with great accuracy, but instead the frequency at which maximum power is consumed by the probe is used to drive the phaco probe under normal operating conditions. Also, the closed-loop feedback control system greatly stabilizes the consistency of the performance of the probe as a function of a stroke length versus applied power command, which is really what the ophthalmic surgeon is truly interested in.

The foregoing detailed description shows that the preferred embodiments of the present invention are well suited to fulfill the objects above-stated. It is recognized that those in the art may make various modifications or additions to the preferred embodiments chosen to illustrate the present invention without departing from the spirit and proper scope of the present invention. For example, transducers having significantly lower or higher resonant frequencies may be utilized, and the control system may be implemented more completely in hard-wired electronic circuits or more completely in digital circuits which minimize the use of analog signals by providing greater software control. Accordingly, it is to be understood that the protection sought and to be afforded hereby should be deemed to extend to the subject matter defined by the appended claims, including all fair equivalents thereof.

We claim:

1. A method for automatically determining the resonant frequency of a surgical instrument powered by an ultrasonic transducer, and for driving the transducer to automatically maintain constant power output, comprising:
   providing an alternating current electric driving signal having a substantially constant voltage amplitude to drive the ultrasonic transducer at each of a plurality of frequencies;
   monitoring electrical power consumed by the instrument by measuring voltage applied to and current drawn by the instrument at each of said plurality of frequencies;
   selecting a dominant frequency by determining which frequency, out of those frequencies which were monitored, had the greatest electrical power consumed by the instrument;
   setting the driving signal at said dominant frequency; and
   driving the ultrasonic transducer at said dominant frequency while automatically varying the voltage amplitude of the driving signal to maintain substantially constant power output independent of changing conditions experienced by the instrument.

2. A method for automatically determining the resonant frequency of a surgical instrument powered by an ultrasonic transducer, and for driving the transducer to maintain constant power output, comprising the steps of:
   providing an alternating current electric driving signal having a substantially constant voltage amplitude to drive the ultrasonic transducer at each of a plurality of frequencies within a given range of frequencies;
   monitoring electrical power consumed by the instrument by measuring voltage applied to and current drawn by the instrument at each of said plurality of frequencies;
   selecting an apparent resonant frequency within the range of frequencies by determining which frequency, out of those frequencies which were monitored, had the greatest electrical power consumed by the instrument;
   comparing the amount of power consumed at the apparent resonant frequency with amounts of power consumed by the instrument at at least a first frequency below the apparent resonant frequency, and at at least a second frequency above the apparent resonant frequency;
   selecting the apparent resonant frequency as the dominant resonant frequency of the instrument at least in part based upon the result of the comparisons performed in said comparing step that the power consumed at each of said first and second frequencies is less than the power at said apparent resonant frequency;
   setting the driving signal at said dominant frequency; and
   driving the ultrasonic transducer at said dominant frequency while varying the voltage amplitude of the driving signal to maintain substantially constant power output.

3. A method as in claim 2 further comprising the step of:
   sweeping the driving signal through said plurality of frequencies during said monitoring step.

4. A method as defined in claim 2 wherein:
   said selecting step includes at least in part detecting that the power consumed at each of the first and second frequencies to be at least a predetermined amount in order to select the apparent resonant frequency as the dominant resonant frequency.

5. The method as in claim 4, wherein:
   said comparing step includes detecting whether the amount of power consumed at a plurality of frequencies decreases with increasing distance from the apparent resonant frequency in order to select the apparent resonant frequency as the dominant resonant frequency.

6. A method as in claim 4, wherein:
   said comparing step further includes comparing the power consumed by the instrument at the apparent resonant frequency against the power consumed by the instrument at a plurality of frequencies below and a plurality of frequencies above an apparent resonant frequency within a band of predetermined size centered about the apparent resonant frequency, and
   said selecting step includes requiring that the power consumed at each of the pluralities of frequencies in the band be at least a predetermined amount in order to select the apparent resonant frequency as the dominant resonant frequency.

7. A method as in claim 2, wherein:
said comparing step further includes (1) comparing the amount of power consumed at the apparent resonant frequency with amounts of power consumed by the instrument at frequencies below the apparent resonant frequency, and at frequencies above the apparent resonant frequency, where the frequencies are a successively greater incremental distance from the apparent resonant frequency, and comparing the power consumed at the instrument with a predetermined value.

8. A method as in claim 7, wherein:
said pluralities of frequencies are within a band of frequencies from about 26 KHz to about 32 KHz;
the first and second frequencies are at least about 100 Hz from the apparent resonant frequency.

9. A method as in claim 2, wherein:
said plurality of frequencies is within a band of frequencies from about 26 KHz to about 32 KHz; and
the first and second frequencies are at least about 100 Hz from the apparent resonant frequency.

10. An electronic control system for determining the dominant resonant frequency of an ophthalmic surgical instrument containing an ultrasonic transducer and for thereafter driving said transducer at its dominant resonant frequency for a constant power output at a specified power level comprising:
means for producing an alternating current ("AC") electrical signal at each of a plurality of frequencies to power the ultrasonic transducer;
means for monitoring electrical power consumed by the transducer from the AC electrical signal at each of said plurality of frequencies;
means for selecting an apparent resonant frequency by determining which frequency within the range of frequencies is the dominant resonant frequency under test conditions;
drive means for generating an AC electrical signal at the selected apparent resonant frequency and for delivering said electrical signal to said transducer; and
automatic closed loop feedback control means, responsive to the means for monitoring, for adjusting the voltage amplitude of the AC electrical signal produced by said drive means to maintain the power consumed by the ultrasonic transducer at a substantially constant level substantially independent of changing conditions experienced by the instrument hen the to substantially continuously achieve the specified power level.

11. The apparatus of claim 10, further comprising:
means for determining whether the frequency at which the transducer appears to consume maximum power is a true peak frequency relative to at least one adjacent frequency above and at least one adjacent frequency below said apparent resonant frequency.

12. An apparatus as in claim 10, wherein:
the drive means includes means for producing electrical signals having a first signal representative of a desired power level;
the means for monitoring includes means for producing a power feedback signal representative of the electrical power being consumed by the transducer; and further comprising:
means for producing an error signal by comparing the power feedback signal representative of the electrical power then being consumed by the transducer and a signal representative of the specified power level.

13. The apparatus of claim 12, wherein:
said drive means includes means responsive to the feedback error signal for adjustably amplifying a first low power electrical signal to produce a higher power electrical signal.

14. The apparatus of claim 13, wherein the means for monitoring monitors apparent electrical power consumed, and includes means for producing a first feedback signal whose amplitude corresponds to the amplitude of the voltage of the AC electrical signal, and means for producing a second feedback signal whose amplitude corresponds to the amplitude of the current of the AC electrical signal, and the means for producing a power feedback signal operates at least in part by combining the first and second feedback signals in order to produce its apparent power signal.

15. The invention as defined in claim 10 wherein said monitoring step comprises detecting output voltage magnitude and detecting output current magnitude.

* * * * *